United States Patent
Cygler

(10) Patent No.: US 9,265,338 B1
(45) Date of Patent: Feb. 23, 2016

(54) ELECTRIC TOOTHBRUSH

(71) Applicant: Harry Cygler, Delray Beach, FL (US)

(72) Inventor: Harry Cygler, Delray Beach, FL (US)

( * ) Notice: Subject to any disclaimer, the term of this patent is extended or adjusted under 35 U.S.C. 154(b) by 0 days.

(21) Appl. No.: 14/834,907

(22) Filed: Aug. 25, 2015

(51) Int. Cl.
| | |
|---|---|
| A46B 13/02 | (2006.01) |
| A61C 17/22 | (2006.01) |
| A61C 17/34 | (2006.01) |
| A46B 15/00 | (2006.01) |

(52) U.S. Cl.
CPC .............. *A46B 13/02* (2013.01); *A46B 15/0071* (2013.01); *A61C 17/222* (2013.01); *A61C 17/225* (2013.01); *A61C 17/227* (2013.01); *A61C 17/349* (2013.01); *A61C 17/22* (2013.01)

(58) Field of Classification Search
CPC ........ A61C 17/22; A61C 17/24; A61C 17/26; A61C 17/222; A61C 17/225; A46B 9/04; A46B 13/02
USPC .............................................. 15/22.1, 28, 105
See application file for complete search history.

(56) References Cited

U.S. PATENT DOCUMENTS

| | | | |
|---|---|---|---|
| 3,072,938 A | 1/1963 | Phaneuf | |
| 3,588,936 A | 6/1971 | Duve | |
| 4,377,877 A | 3/1983 | O'Rourke | |
| 5,495,632 A * | 3/1996 | Baker | A46B 13/02 15/23 |
| 5,504,959 A | 4/1996 | Yukawa | |
| D388,958 S | 1/1998 | Hartwein | |
| 6,047,711 A | 4/2000 | Wagner | |
| 6,058,542 A * | 5/2000 | Lo | A46B 9/02 15/22.1 |
| 6,766,548 B1 | 7/2004 | Lukas | |
| 7,168,121 B2 | 1/2007 | Rehkemper | |
| 2002/0104177 A1 * | 8/2002 | Wong | A46B 13/008 15/28 |
| 2006/0005330 A1 * | 1/2006 | Rehkemper | A61C 17/225 15/22.1 |
| 2013/0061412 A1 * | 3/2013 | Vashi | A46B 5/0095 15/106 |

FOREIGN PATENT DOCUMENTS

CN 203220449 10/2013

* cited by examiner

*Primary Examiner* — Michael Jennings
(74) *Attorney, Agent, or Firm* — Kyle A. Fletcher, Esq.

(57) ABSTRACT

The electric toothbrush is constructed of a first portion and a second portion. The first portion is able to pivot with respect to the second portion via a hinge. The first portion houses componentry associated with the toothbrush. The second portion includes a floss dispenser on a distal end, and is used as a handle for the electric toothbrush. The first portion includes at least one rotating head that includes bristles adapted to brush teeth. The at least one rotating head is in mechanical connection with a bevel gear. The bevel gear is in mechanical connection with a motor via a drive shaft. The motor is in wired connection with a switch and at least one battery.

10 Claims, 3 Drawing Sheets

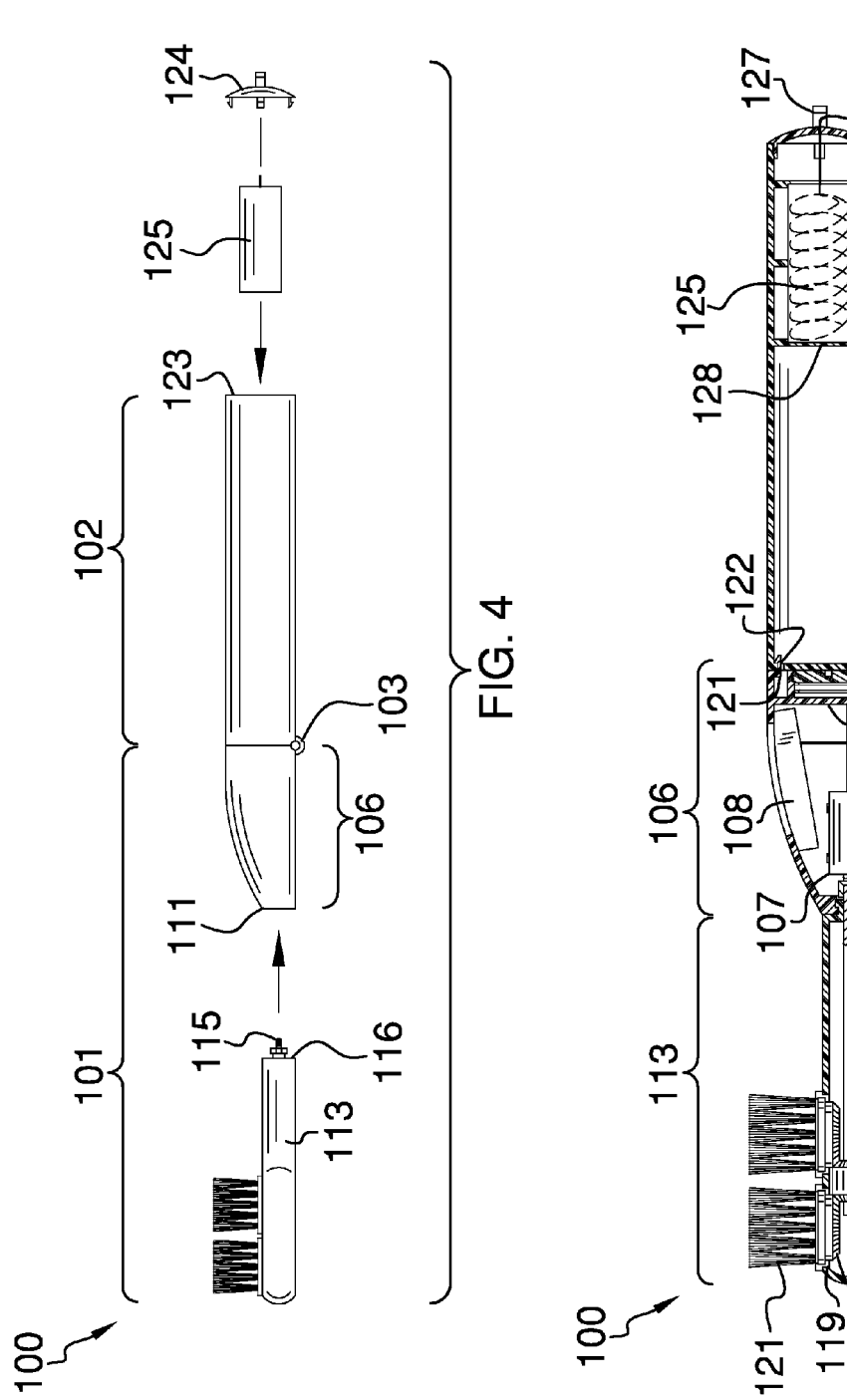

ELECTRIC TOOTHBRUSH

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

The present invention relates to the field of electric toothbrushes, more specifically, an electronic toothbrush that is able to fold up for storage when not in use.

Electronic toothbrushes have been around for quite some time, and aid in cleaning teeth. However, electronic toothbrushes are bulky in size, which can be problematic when traveling. What is needed and is accomplished in this patent application is an electric toothbrush that is able to collapse onto itself when not in use, and which includes a floss dispenser on a distal end.

SUMMARY OF INVENTION

The electric toothbrush is constructed of a first portion and a second portion. The first portion is able to pivot with respect to the second portion via a hinge. The first portion houses componentry associated with toothbrush. The second portion includes a floss dispenser on a distal end, and is used as a handle for the electric toothbrush. The first portion includes at least one rotating head that includes bristles adapted to brush teeth. The at least one rotating head is in mechanical connection with a bevel gear. The bevel gear is in mechanical connection with a motor via a drive shaft. The motor is in wired connection with a switch and at least one battery.

An object of the invention is to provide an electric toothbrush that is able to fold up when not in use.

A further object of the invention is to provide a second portion that is a handle, and which pivots via a hinge with a first portion that includes componentry associated with the electric toothbrush.

An even further object of the invention is for the second portion to be aligned linearly with the first portion or to rotate 180 degree in adjacency of the first portion.

An even further object of the invention is to provide a floss dispenser on a distal end of the second portion.

These together with additional objects, features and advantages of the electric toothbrush will be readily apparent to those of ordinary skill in the art upon reading the following detailed description of the presently preferred, but nonetheless illustrative, embodiments when taken in conjunction with the accompanying drawings.

In this respect, before explaining the current embodiments of the electric toothbrush in detail, it is to be understood that the electric toothbrush is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the electric toothbrush.

It is therefore important that the claims be regarded as including such equivalent construction insofar as they do not depart from the spirit and scope of the electric toothbrush. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 4 is an exploded, side view of an embodiment of the disclosure.

FIG. 5 is a cross-sectional view of an embodiment of the disclosure across line 5-5 in FIG. 2.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
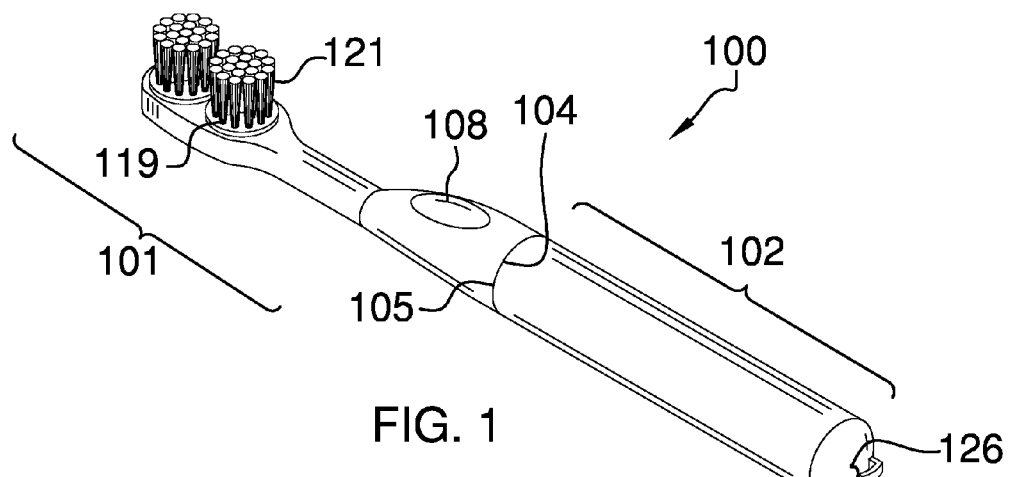
FIG. 1 is a perspective view of an embodiment of the disclosure.
Figure 2:
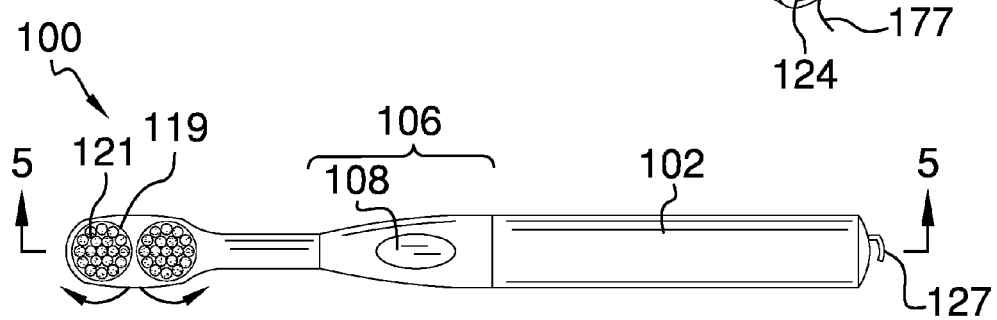
FIG. 2 is a top view of an embodiment of the disclosure.
Figure 3:
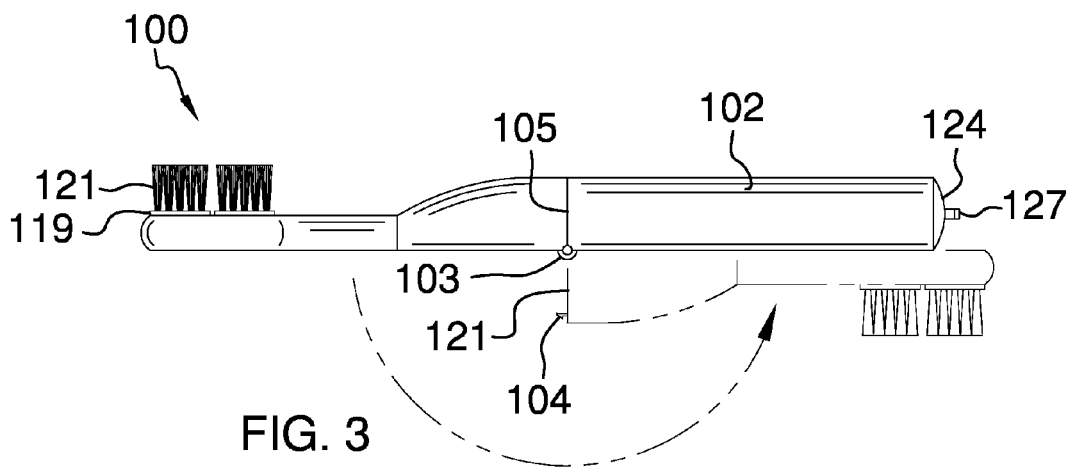
FIG. 3 is a side view of an embodiment of the disclosure.
Figure 6:
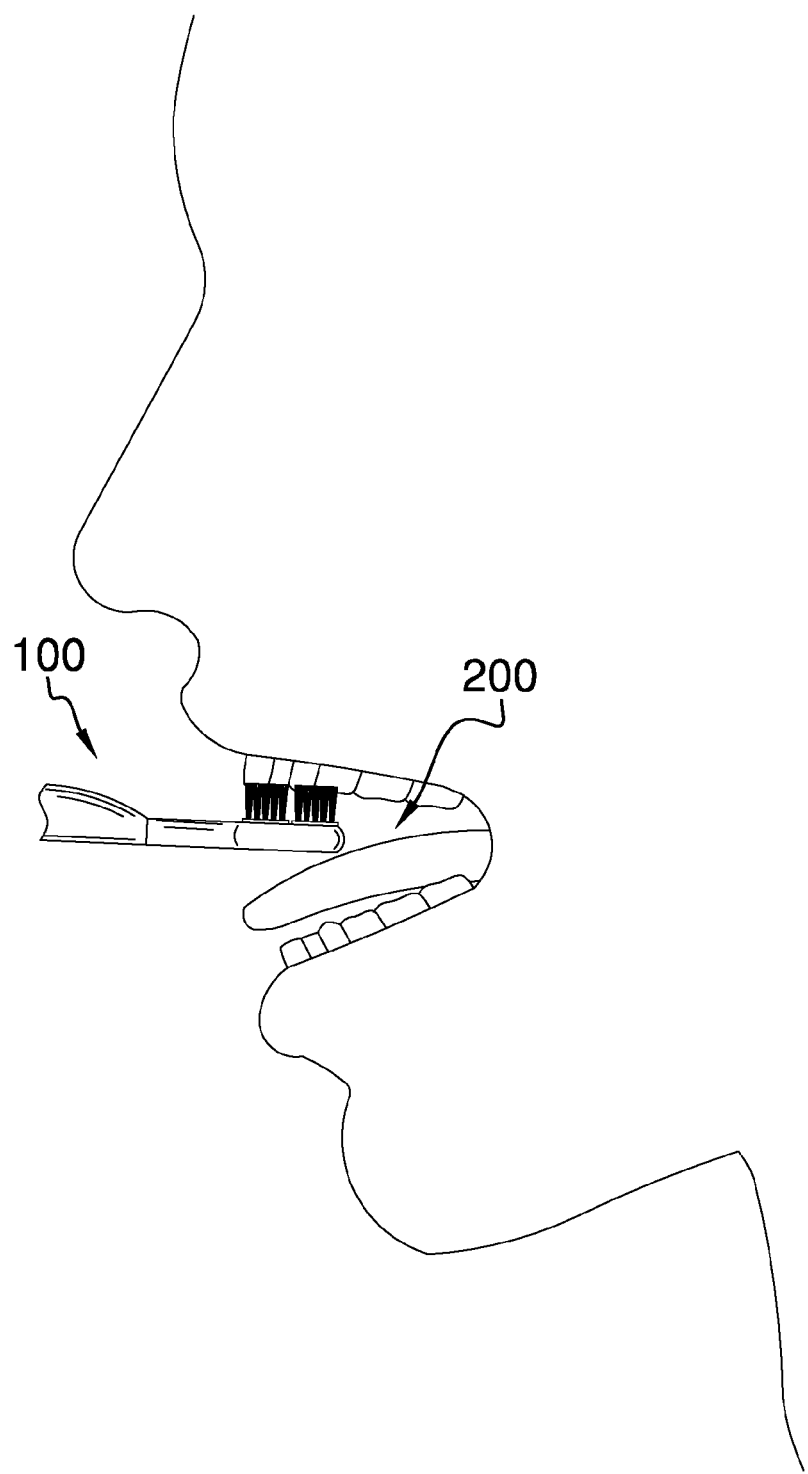
FIG. 6 is a side view of an embodiment of the disclosure in use.

Detailed reference will now be made to a first potential embodiment of the disclosure, which is illustrated in FIGS. 1 through 6. The electric toothbrush 100 (hereinafter invention) comprises a first portion 101 and a second portion 102. The first portion 101 is connected to and able to pivot with respect to the second portion 102 via a hinge 103. The first portion 101 is further defined with a first distal end 104, whereas the second portion is further defined with a second distal end 105. The hinge 103 connects the first portion 101 at the first distal end 104 as well as the second portion 102 at the second distal end 105. The hinge 103 enables the first portion 101 to rotate from 0 to 180 degrees with respect to the second portion 102. The second portion 102 is a hollowed cylinder.

The first portion 101 is further defined with a motor portion 106 that is of hollowed construction, and houses a motor 107, a switch 108, and a battery compartment 109. The battery compartment 109 includes at least one battery 110. The battery compartment 109 is adjacent to the first distal end 104. The at least one battery 110 is in wired connection with the switch 108. The switch 108 is also in wired connection with the motor 107. The motor portion 106 is further defined with a motor drive surface 111, which is opposite of the first distal end 104. The motor drive surface 111 includes a drive shaft receptacle 112 thereon. The first portion 101 is further defined with a brush head portion 113.

The brush head portion 113 and the motor portion 106 make up the entire first portion 101. Moreover, the brush head portion 113 includes a drive shaft 114 with a twist lock connection 115. The twist lock connection 115 is able to connect with the drive shaft receptacle 112 of the motor portion 106 thereby connecting the brush head portion 113. The brush head portion 113 is replaceable, and may be a part of a set that can be interchanged as needed. Moreover, the twist lock connection 115 extends from a brush head distal end 116 of the brush head portion 113. The brush head distal end 116 is able to interface with the motor drive surface 111 when the brush head portion 113 is connected to the motor portion 106.

The brush head portion 113, like the motor portion 106, is of hollowed construction. The brush head portion 113 includes a bevel gear 117 that is rotated via the drive shaft 114. The bevel gear 117 is supported via a bevel armature 118. The bevel gear 117 is in mechanical connection with at least one rotating head 119. The at least one rotating head 119 includes a head gear 120 that connects with and rotates in concert with the bevel gear 117. The at least one rotating head 119 includes bristles 121 that extend perpendicularly with respect to the drive shaft 114. The bristles 121 are adapted to brush teeth and surfaces inside of a mouth 200, and are well known in the art.

The first distal end 104 of the first portion 101 includes a locking clip 121. The locking clip 121 engages a clip notch 122 provided in the second distal end 105 of the second portion 102. The locking clip 121 enables the first portion 101 to be locked in linear relationship with the second portion 102. The second portion 102 is further defined with a third distal end 123. The third distal end 123 is opposite the second distal end 105.

The third distal end 123 includes a removable cap 124. The removable cap 124 is removed from the second portion 102 in order for a floss cartridge 125 to be inserted and replaced as needed. The removable cap 124 includes a floss hole 126 that enables floss 177 to extend out of the second portion 102. The removable cap 124 includes a floss cutter armature 127. The floss cutter armature 127 is well known in the art of dental floss. The second portion 102 is of hollowed construction, and includes a floss partition 128 that limits the travel of the floss cartridge 125 into the second portion 102.

With respect to the above description, it is to be realized that the optimum dimensional relationship for the various components of the invention described above and in FIGS. 1 through 6, include variations in size, materials, shape, form function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. An electric toothbrush comprising:
   a first portion that includes at least one rotating head with bristles thereon;
   wherein said bristles are adapted to brush teeth and inside of a mouth;
   wherein the first portion is able to pivot with respect to a second portion via a hinge;
   wherein the first portion is further defined with a first distal end, whereas the second portion is further defined with a second distal end;
   wherein the hinge connects the first portion at the first distal end as well as the second portion at the second distal end;
   wherein the hinge enables the first portion to rotate from 0 to 180 degrees with respect to the second portion;
   wherein the second portion is a cylinder of hollow construction, and is adapted to be grabbed when in use in brushing said mouth;
   wherein the first portion is further defined with a motor portion that is of hollowed construction, and houses a motor, a switch, and a battery compartment;
   wherein the battery compartment includes at least one battery; wherein the battery compartment is adjacent to the first distal end;
   wherein the at least one battery is in wired connection with the switch; wherein the switch is also in wired connection with the motor;
   wherein the motor portion is further defined with a motor drive surface, which is opposite of the first distal end;
   wherein the motor drive surface includes a drive shaft receptacle thereon; wherein the first portion is further defined with a brush head portion;
   wherein the brush head portion and the motor portion make up the entire first portion;
   wherein the brush head portion includes a drive shaft with a twist lock connection; wherein the twist lock connection is able to connect with the drive shaft receptacle of the motor portion thereby connecting the brush head portion.

2. The electric toothbrush according to claim 1 wherein the twist lock connection extends from a brush head distal end of the brush head portion; wherein the brush head distal end is able to interface with the motor drive surface when the brush head portion is connected to the motor portion.

3. The electric toothbrush according to claim 2 wherein the brush head portion is, of hollowed construction.

4. The electric toothbrush according to claim 3 wherein the brush head portion includes a bevel gear that is rotated via the drive shaft; wherein the bevel gear is supported via a bevel armature.

5. The electric toothbrush according to claim 4 wherein the bevel gear is in mechanical connection with the at least one rotating head; wherein the at least one rotating head includes a head gear that connects with and rotates in concert with the bevel gear.

6. The electric toothbrush according to claim 5 wherein the at least one rotating head includes the bristles that extend perpendicularly with respect to the drive shaft.

7. The electric toothbrush according to claim 6 wherein the first distal end of the first portion includes a locking clip; wherein the locking clip engages a clip notch provided in the second distal end of the second portion.

8. The electric toothbrush according to claim 7 wherein the locking clip enables the first portion to be locked in linear relationship with the second portion.

9. The electric toothbrush according to claim 8 wherein the second portion is further defined with a third distal end; wherein the third distal end is opposite the second distal end.

10. The electric toothbrush according to claim 9 wherein the third distal end includes a removable cap; wherein the removable cap is removed from the second portion in order for a floss cartridge to be inserted and replaced as needed; wherein the removable cap includes a floss hole that enables floss to extend out of the second portion; wherein the removable cap includes a floss cutter armature; wherein the second portion includes a floss partition that limits the travel of the floss cartridge into the second portion.

\* \* \* \* \*